(12) United States Patent
Neushul et al.

(10) Patent No.: US 9,001,964 B2
(45) Date of Patent: Apr. 7, 2015

(54) COMPUTED TOMOGRAPHY AND TOMOSYNTHESIS SYSTEM

(75) Inventors: Stephen Neushul, Rancho Palos Verdes, CA (US); Matthew Changala, Huntington Beach, CA (US)

(73) Assignee: ICRCO, Inc., Goleta, CA (US)

( * ) Notice: Subject to any disclaimer, the term of this patent is extended or adjusted under 35 U.S.C. 154(b) by 308 days.

(21) Appl. No.: 13/304,617

(22) Filed: Nov. 26, 2011

(65) Prior Publication Data

US 2012/0189094 A1     Jul. 26, 2012

Related U.S. Application Data

(60) Provisional application No. 61/417,421, filed on Nov. 27, 2010.

(51) Int. Cl.
| | |
|---|---|
| *A61B 6/03* | (2006.01) |
| *A61B 6/02* | (2006.01) |
| *A61B 6/00* | (2006.01) |

(52) U.S. Cl.
CPC .............. *A61B 6/035* (2013.01); *A61B 6/027* (2013.01); *A61B 6/4266* (2013.01); *A61B 6/466* (2013.01); *A61B 6/508* (2013.01)

(58) Field of Classification Search
USPC ....................................... 378/4, 15, 19, 21, 22
See application file for complete search history.

(56) References Cited

U.S. PATENT DOCUMENTS

| | | | |
|---|---|---|---|
| 7,020,233 B1 * | 3/2006 | Tybinkowski et al. ............ 378/4 |
| 2004/0264627 A1 * | 12/2004 | Besson ............................. 378/5 |
| 2006/0261296 A1 * | 11/2006 | Heath et al. .................... 250/580 |
| 2010/0243925 A1 * | 9/2010 | Boutet et al. .................. 250/584 |

* cited by examiner

*Primary Examiner* — Glen Kao

(74) *Attorney, Agent, or Firm* — Rowlett Law Firm; Robert D. Rowlett

(57) ABSTRACT

A computed tomography system, capable of tomosynthesis, includes an inner circular gantry and an outer gantry within a housing assembly. A plurality of spaced apart radiology imaging plates are located along the inner gantry and adapted as x-ray detectors. An x-ray source is secured to the outer gantry and adapted to shoot x-rays between the spaced apart detectors and onto the patient or object while being rotated along the gantry and relative to the patient. A radiography device is moveably coupled to the inner gantry and adapted to scan and read the radiology plates and provide the data to an image processing computer. The x-ray source coupled to the outer gantry moves relative to the imaging plates such that a large number of projections can be exposed and thereafter scanned by the integral radiology device.

20 Claims, 15 Drawing Sheets

COMPUTED TOMOGRAPHY AND TOMOSYNTHESIS SYSTEM

CROSS REFERENCE TO RELATED APPLICATION

This application claims the benefit of U.S. Provisional Application No. 61/417,421 filed Nov. 27, 2010, entitled, *Spiral Tomosynthesis And Computed Tomography System Using Photostimulable Storage Phosphor.*

BACKGROUND OF THE INVENTION

1. Field of the Invention

The present invention relates to computed tomography imaging systems and techniques, and more particularly to novel computed tomography and tomosynthesis systems and methods.

2. Background

Projection x-ray imaging is a widely performed diagnostic imaging procedure for producing two dimensional images. Such images are commonly acquired using computed radiography ("CR") or direct digital radiography ("DR") systems. Projection x-ray imaging, however, suffers from the fundamental limitation that three-dimensional anatomic structures are superimposed in the two-dimensional projection image such that overlying structures often obscure the visibility of an underlying structure of interest.

X-ray computed tomography ("CT") was developed, at least in part, to enable the visualization of adjacent anatomic structures in cross-sectional slices through a patient. In conventional geometric CT, the x-ray tube and imaging detector are spaced apart on opposite sides of the patient. The x-ray tube and detector are synchronously moved completely (or near completely) around the patient during the x-ray exposure so the detectors (film, plates, or other detectors) follow and capture the exposures. Conventional CT produces a plane of images in focus at the focal plane of motion and all other locations within the image both above and below the focal plane are generally out of focus and thus blurred and less visible in the resulting image. X-ray CT techniques are known for high patient dose, long exposure and image acquisition times and high procedure cost.

Tomosynthesis is a more recent improvement over conventional projection x-ray imaging, particularly for certain applications. Similar to conventional CT, tomosynthesis combines x-ray exposure and capture and processing with the x-ray/detector techniques generally used in more recent conventional CT. Thus, the x-ray source and x-ray detector arc similarly located on opposite sides of the patient and the x-ray the and detector also move synchronously and continuously about a fulcrum residing in the plane of interest. In contrast to conventional CT, however, the movement around the patient using tomosynthesis is generally much more limited. Tomosynthesis typically uses a small rotation angle of the x-ray head and a smaller number of x-ray exposures to obtain a limited set of data. This limited data is then digitally processed to yield the desired images. Advantages of tomosynthesis over CT include reduced imaging and acquisition time and reduced radiation exposure.

Tomosynthesis allows the digital reconstruction of a generally arbitrary number of cross-sectional tomographic slices through an object from a limited number of acquired projection x-ray images to produce a three-dimensional perspective. The position and thickness of the tomographic slices can be varied in order to achieve better visualization overlapping anatomic structures or to control other aspects of the diagnosis.

Current CT and tomosynthesis systems, however, remain limited in application. For example, conventional tomosynthesis equipment and techniques require the patient to remain still during the exposure process. Remaining still during the exposure and detection period can be challenging for many patients. In mammography techniques a positioning mechanism is used to secure the breast stationary during the exposure process. While the technique allows for detailed imaging, patients often complain of pain and discomfort resulting from the positioning mechanism. What is needed is a tomography and tomosynthesis device capable of making the necessary x-ray exposure quickly so as to shorten the time necessary for the patient to remain still or be secured by a positioning mechanism.

Another disadvantage of currently available CT and computed tomosynthesis systems is their limited availability due to, among other reasons, high initial and operating costs as well as the need for highly trained operators. CT and tomosynthesis systems may not be as readily available in areas lacking the resources to fund such systems. Thus, what is also needed is CT and tomosynthesis systems that are simpler, less complex and less expensive to manufacture and operate. In this way, advanced imaging can provided at more reasonably pricing so as to be made available to less affluent medical centers as well as reducing operating and maintenance costs.

SUMMARY

The present invention is directed to a computed tomography imaging system for scanning a three-dimensional object, such as a patient or a non-object. The computed tomography system only requires a limited number of projection x-ray images and reconstructs those selected cross-sectional tomographic slices through the desired region of interest. By only requiring a limited region of x-ray exposure locations and perspectives, the present invention further provides for a novel computed tomosynthesis system, including a helical tomosynthesis system.

The computed tomography system includes an x-ray radiation source, such as a cone beam x-ray source configured to move incrementally about an arc around the object. A plurality of spaced apart storage phosphor plates are secured on outer surface of an inner rotating hoop assembly. This inner hoop assembly is supported within a gantry assembly or outer housing and defines an inner tubular cavity adapted to receive a patient or object for diagnosis. The phosphor surfaces act as x-ray detectors to acquire and store the projection x-ray energy from the x-ray source. In one embodiment, the phosphor surfaces are placed in a spiral arrangement along the outer surface of the inner hoop so that multiple x-ray images can be continuously acquired in real-time.

A radiography device capable of acquiring image data stored on the storage phosphor surface 12 is secured within the gantry housing and adapted to scan and acquire images from each photostimulable phosphor surface.

As noted, the x-ray source is also moveable about the acquisition arc and, at each x-ray position a projection x-ray image may be taken by energizing the x-ray source and allowing the phosphor surface positioned opposite the x-ray source to acquire that energy passing through the object. As the x-ray source rotates to the next position along the acquisition arc, the inner hoop assembly and storage phosphor surfaces are advanced and rotated such that the next projection x-ray image is exposed on a further portion of the phosphor surface or even another storage phosphor surface. For longer arc x-ray travel, the storage phosphor surfaces, include spaced regions to allow passage of the x-rays. After sufficient phosphor surfaces are exposed to x-rays, or preferably while other surfaces are being exposed, the inner hoop assembly is rotated such that the exposed phosphor surfaces are rotated adjacent the radiography device and the projection x-ray images are acquired. In this way, a large number of projections can be continuously exposed without delay and the images acquired thereafter in a very short period of time. In an alternative embodiment, the radiographic imaging device scans and reads a previously excited photostimulable phosphor surface and acquires an image concurrently while the inner hoop assembly is rotating for another x-ray exposure. In this fashion, the acquired images are processed and available in real time.

Various reconstruction algorithms may be used to reconstruct tomographic cross-sections from the acquired projection images as is known. The present system provides tomosynthesis images with increased visibility of adjacent structures by removal of overlying anatomy and, compared to conventional CT, is less expensive, more reliable, easier to install and easier to use.

Currently, longer x-ray exposure times are detrimental to the image acquisition process. The extended times increase the possibility that the patient will move during the study. Shifting or changing position during exposure causes distortions in the final image. The tomosynthesis system of the present invention acquires images in rapid succession without need to wait for processing before taking the next image. This decreases the probability of the patient shifting during the exposure and acquisition process. As a result, the system of the present invention is able to acquire images from a greater variety of anatomical positions including; chest, hip, lumbar, upper and lower extremity images than presently available.

In a particular embodiment of the present invention, the computed tomography system comprising a tubular imaging assembly having an inner hoop assembly positioned within a larger outer hoop assembly. A pair of opposing side plates connects the two hoop assemblies together and are adapted to allow the inner hoop assembly to rotate relative to the outer hoop assembly and sides. A plurality of sliding surfaces and wheels mounted to the side walls may be used to support the inner hoop assembly and provide for the rotational movement. A drive assembly coupled to the inner hoop assembly provides the rotational movement. The inner and outer hoop assemblies and side walls generally form Or support the gantry housing and form a tubular cavity. The imaging assembly or gantry housing is adapted for receiving and passing an object within the tubular cavity inside the inner hoop assembly, which is rotatable relative to the outer hoop assembly and gantry housing.

An x-ray source is coupled to the imaging assembly and adapted for emitting x-ray energy through the patient. The x-ray source is moveable through an arc allowing x-ray exposure of the patient through an arc of zero to sixty degrees. The x-ray source may be a conventional x-ray tube emitting a fan or cone beam.

The generally flat outer surface of the inner hoop assembly or hoop assembly is covered with a plurality of spaced apart storage phosphor surfaces (although a continuous surface may be used) with the exposure surfaces facing inwardly within the tubular cavity. The phosphor surfaces are adapted to receive the x-rays passing thought the object.

An image acquisition device or radiography device, such as a digital radiography, or computed radiography. The image acquisition device or devices is (are) adapted for scanning the storage phosphor surfaces when the inner hoop assembly is rotated so as to acquire the stored images. The acquisition device preferably erases the storage phosphor after acquiring the stored image such that it is ready to receive the next x-ray. Alternatively, more recently available panel detector may be directly coupled to the inner hoop assembly generally eliminating the need for the radiography device.

BRIEF DESCRIPTION OF THE DRAWINGS

FIGS. 11A through 111C show a side, front and top view of the embodiment of the present invention shown in FIG. 10.

DETAILED DESCRIPTION OF THE PREFERRED EMBODIMENTS

Figure 1:
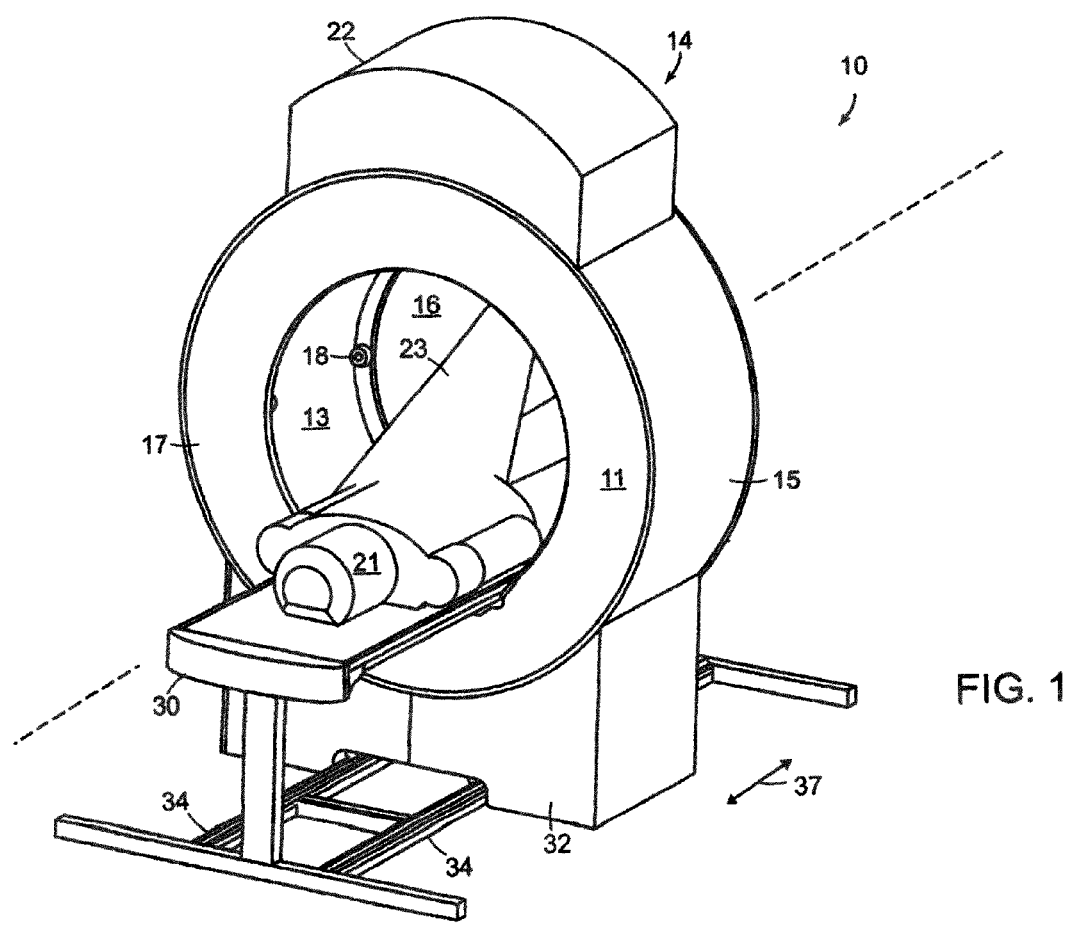
FIG. 1 shows a perspective view of an embodiment of the present invention with an object (patient) positioned on the patient table within the imaging gantry assembly.
Figure 2:
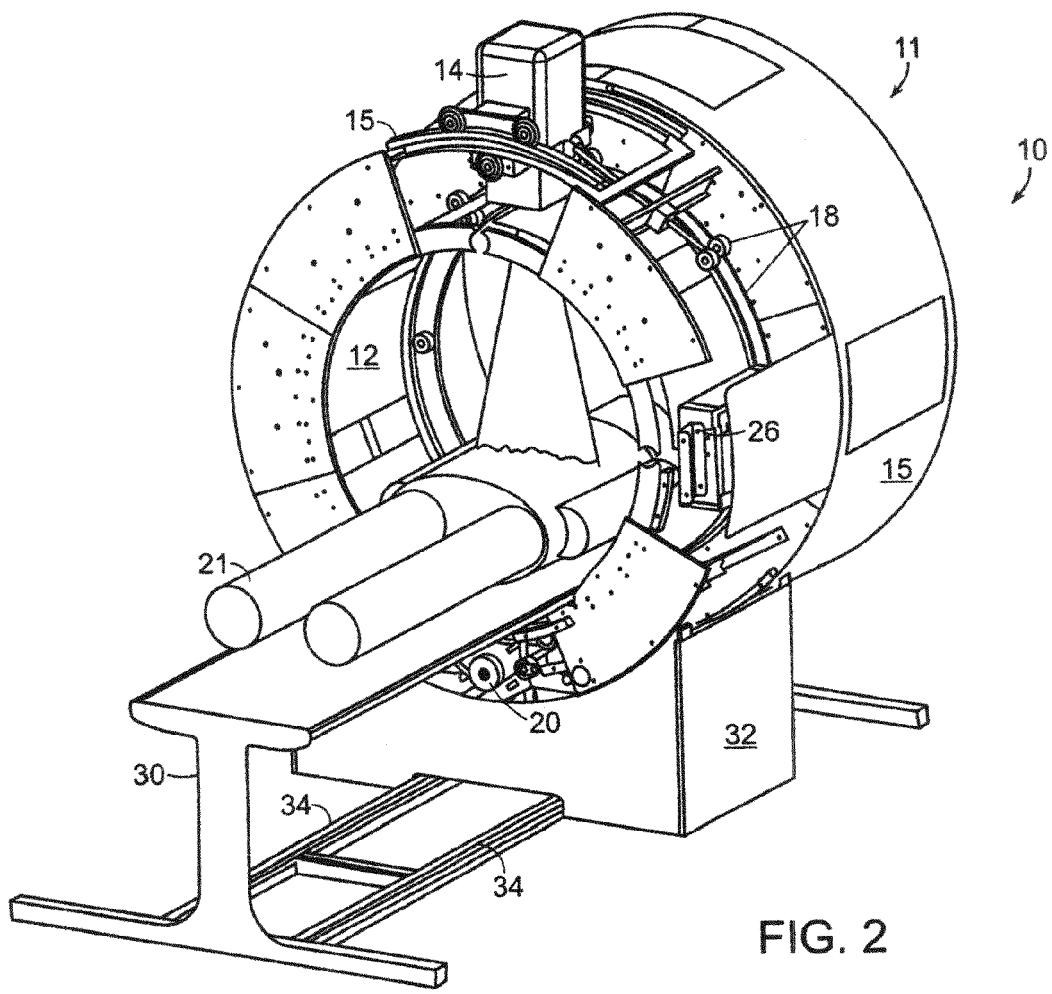
FIG. 2 shows a partial exploded view of an embodiment of the present invention with a patient positioned on the patient table within the imaging gantry assembly.

Referring now to FIGS. 1 and 2, an embodiment of the computed tomography imaging system 10 of the present invention shown. The computed tomography system includes a tubular gantry housing assembly 11 (also referred to as the imaging assembly), which is preferably supported by a base assembly 23, though this may be an integral member. The gantry housing assembly includes an inner cylinder or hoop assembly 13 defining an inner tubular cavity 16. The inner hoop assembly 13 is positioned within a larger outer cylinder or outer hoop assembly 15 concentrically along a perpendicular axis 27 passing through the tubular cavity 16. The outer hoop assembly 215 includes a cover or outer housing surface as shown in FIGS. 1 and 2. A pair of opposing sides 17 completes the outer gantry housing 11 and couples the inner hoop assembly 12 and the outer hoop assembly 15. The gantry housing is adapted to allow the inner hoop assembly 13 to rotate relative to the outer hoop assembly 15 and sides 17. A generally frictionless surface and preferably utilizing sliding or rolling members 18 may be mounted to the side walls 17 and adapted to support the inner hoop assembly 13 while allowing rotational movement about the common perpendicular axis within the tubular cavity. A drive assembly 20 (FIG. 7) is coupled to the inner hoop assembly 13 and provides the rotational movement of the inner hoop assembly. The inner and outer hoop assemblies 13, 15 and side walls 17 define a tubular open space 19 there between. The tubular cavity 16 within the gantry housing 11 is adapted for receiving and passing an object 21, such as a patient, including a veterinary patient or a non-living object, within the inner hoop assembly 13 as shown. The inner hoop assembly 13, or a portion thereof, may include an inside cover that is fixed to the gantry housing 11 or sides 17, and adapted to protect the object 21 from the rotating inner hoop assembly or the rotating union between.

Figures 7, 8:
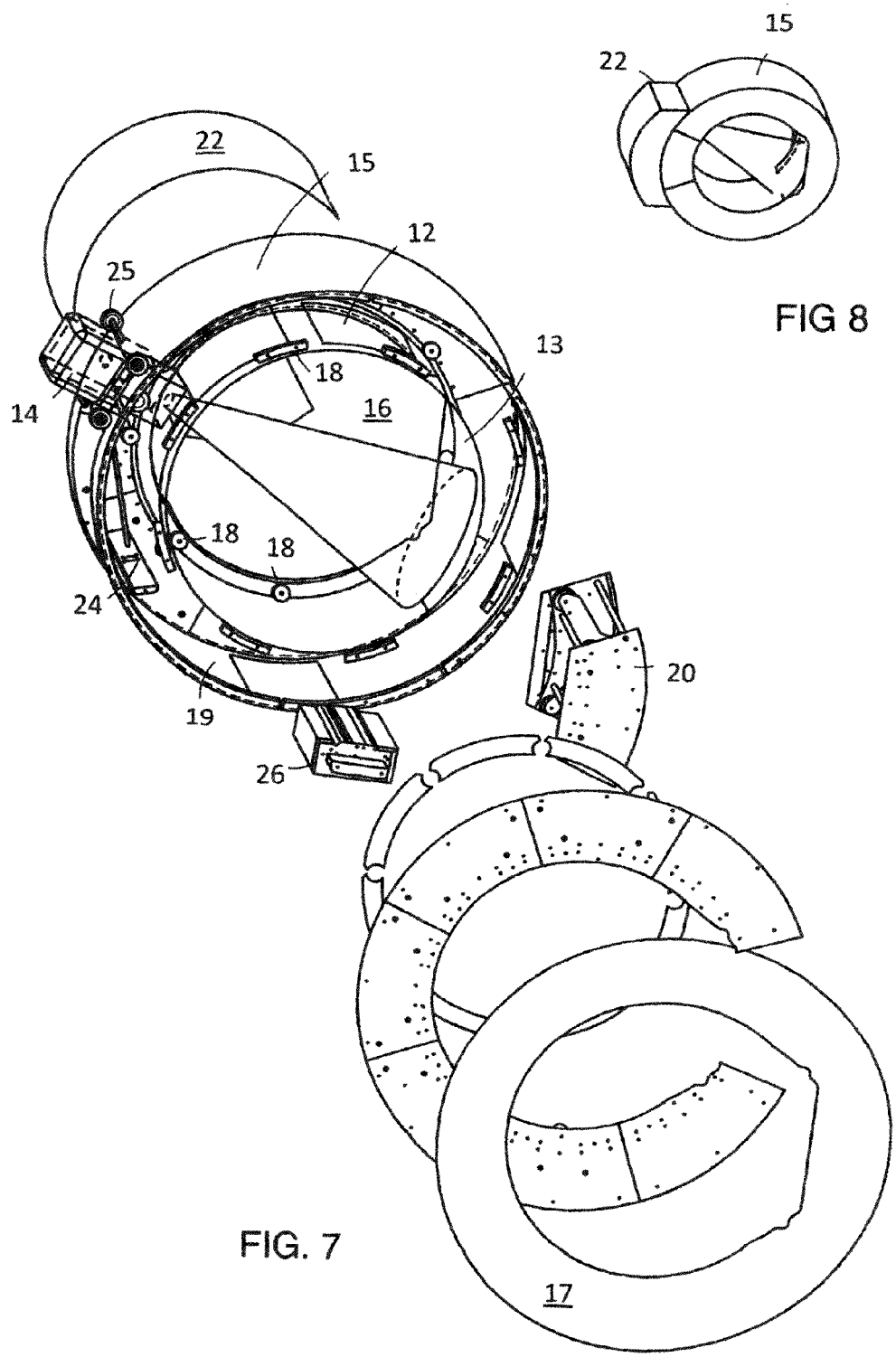
FIG. 7 is a partial exploded view of an embodiment of the present invention.
FIG. 8 is a perspective view of the gantry housing assembly of an embodiment of the present invention.
Figure 9A:
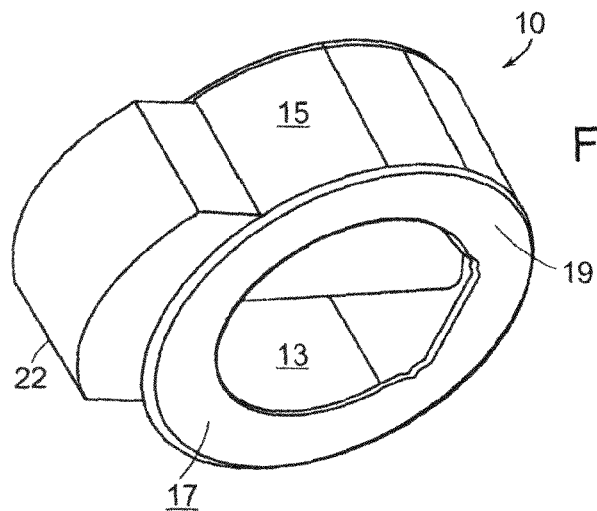
FIGS. 9A through 9D show various perspective views of the gantry housing assembly of an embodiment of the present invention.
Figure 9B:
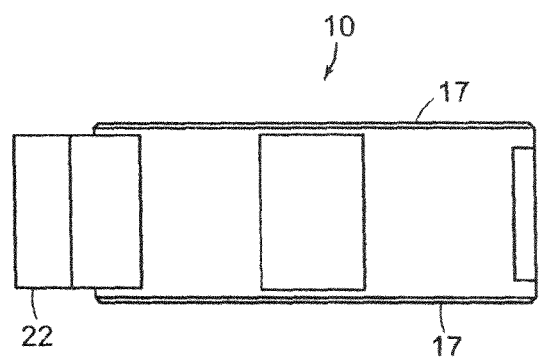
Figure 9C:
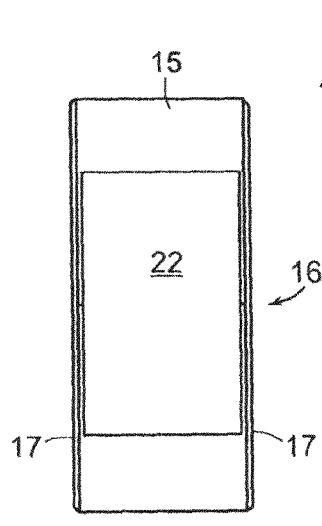
Figure 9D:
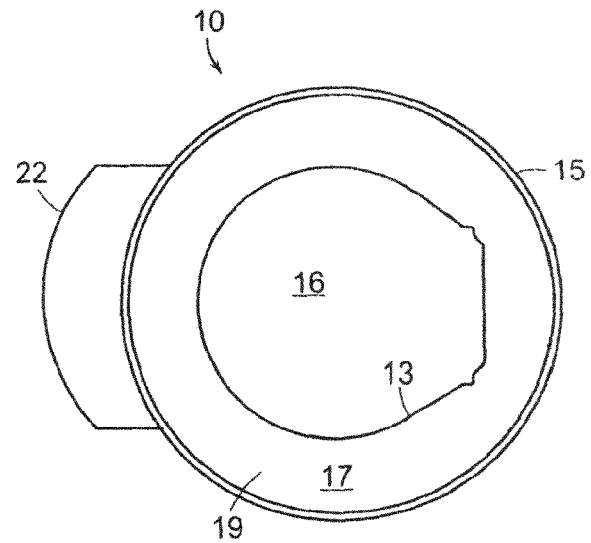
Figure 10:
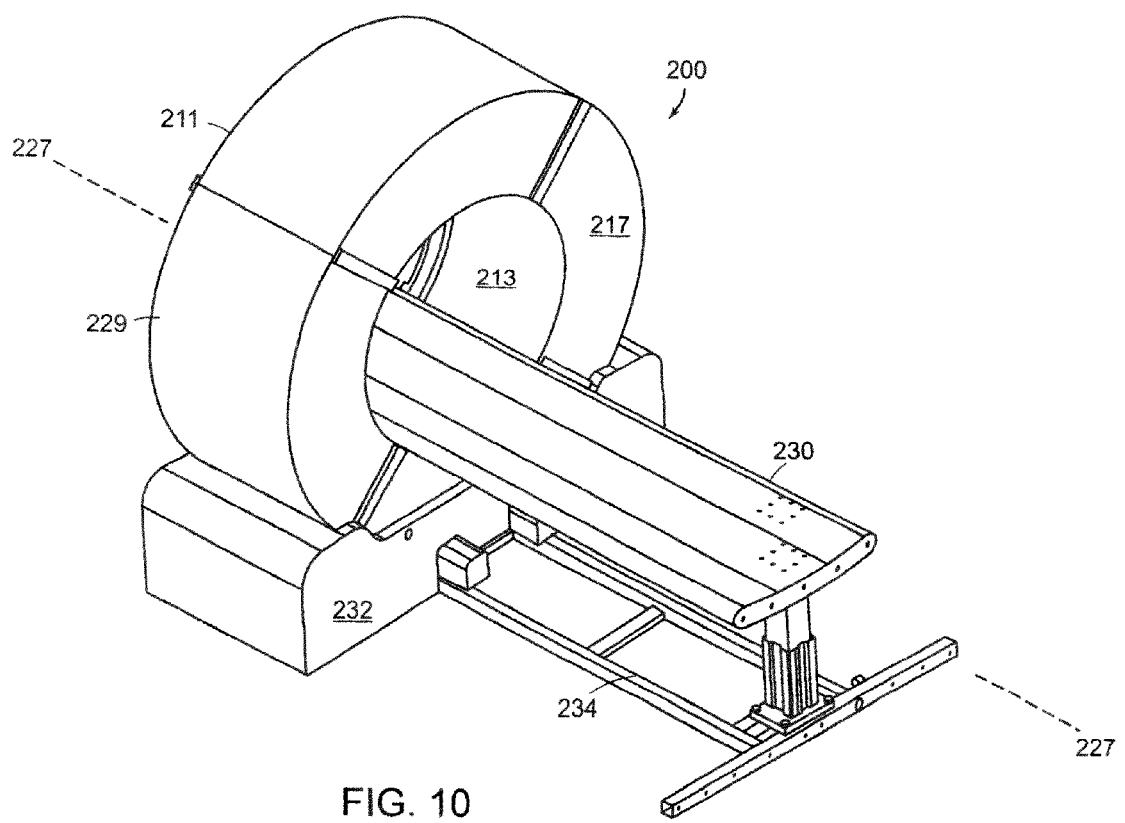
FIG. 10 is a perspective view of a preferred embodiment of present invention.
Figure 11A:
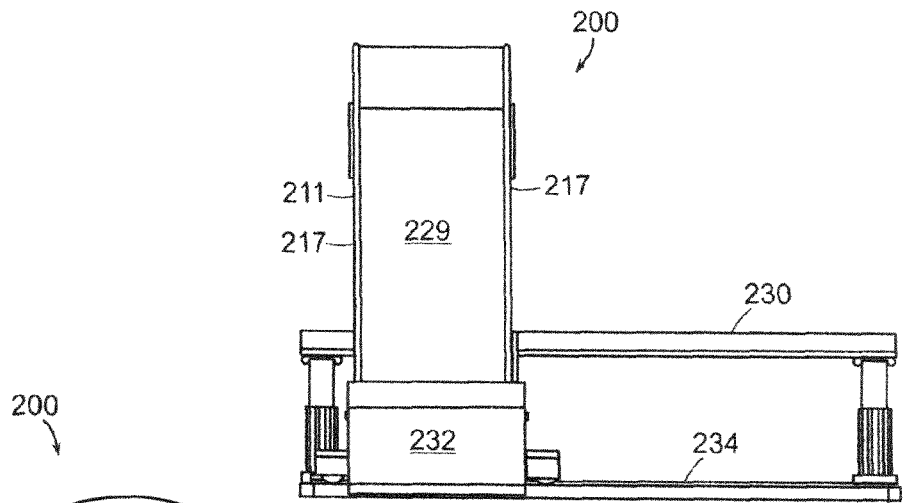
Figure 11B:
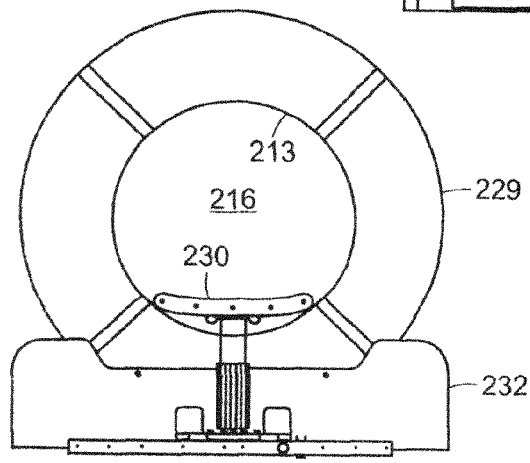
Figure 11C:
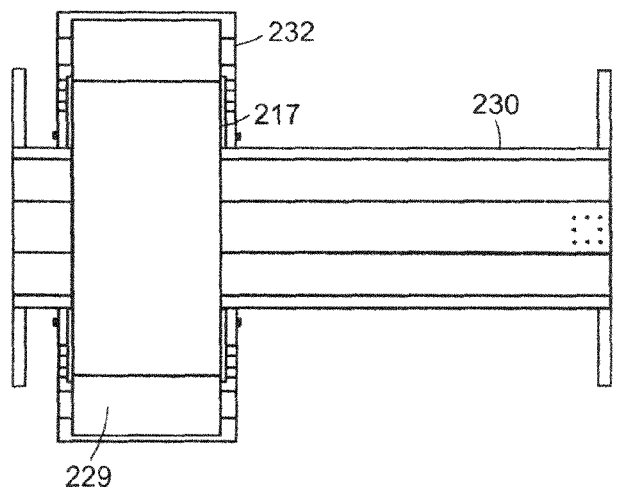

An x-ray source 14 is coupled to the gantry assembly 11 and adapted for emitting x-ray energy through the object 21. In the embodiment shown, the x-ray source is mounted above and outside the cover portion of the outer hoop assembly 15 and adapted to travel about a supporting track portion of outer hoop assembly along an arc 25 generally concentric with the perpendicular axis 27. A cover 22 is used to cover and protect the x-ray source 14. The cover is mounted to the x-ray source and adapted to either move with the x-ray source or mounted to gantry 11 or outer hoop assembly 15 and adapted to provide sufficient travel for x-ray source about arc 25. The x-ray source 14 is moveable through an arc (FIG. 4) allowing x-ray exposure or emitting an x-ray beam 23 through the object or patient 21. Preferably, the x-ray device 14 is moveably coupled to the gantry assembly 11 so it can be moved along arc 25 from about zero to sixty degrees as shown in FIG. 4. As shown in FIG. 8, an x-ray tube motor and holder 24 and drive mechanism 25 provides for the x-ray device 14 to be moved about the inner hoop assembly 13 through the defined arc. The drive mechanism 25 may include a gear and track assembly or any other method providing for precise movement along an arc.

The x-ray source 14 may be conventional, fan beam or preferably, a cone beam 23 and may be directed through a plurality of slots in the inner hoop assembly 13 and between storage phosphor surfaces 12. Alternatively, the inner hoop assembly 13, at least between the phosphor plates or surfaces 12 may be made from materials translucent to x-rays or modified to provide a desired effect to the beam 23. As shown in FIG. 4C the spacing between imaging plates or surfaces 12 may be used as a collimator 27 or alternatively and preferably, a fixed collimator may be provided to properly shape the x-ray beam 23.

The generally flat outer surface of the inner hoop assembly 13 is covered with a plurality of spaced apart storage phosphor surfaces 12 (although a continuous surface may be used) that are exposed within the tubular cavity 19. Preferably, the tubular cavity 19 is maintained free from ambient light during the image acquisition process. The phosphor surfaces 12 are adapted to receive the x-rays passing thought the patient 21.

An image acquisition device 26, such as a DR or scanning CR is coupled to the imaging assembly 11 and preferably to the side walls 17. The image acquisition device 26 or devices as a plurality may be used to increase image acquisition speed, is (are) adapted for scanning the storage phosphor surfaces 12 when the inner hoop assembly 13 is rotated so as to acquire the stored images. The acquisition device 26 preferably erases the storage phosphor 12 after acquiring the stored image such that it is ready to receive the next x-ray 21.

In the preferred embodiment, the radiographic imaging device 26 or at least one of them in a multiple imaging device embodiment of the present invention is a scanning head radiography device such as one made by iCRco of Torrance, Calif. and described in U.S. patent application Ser. No. 12/197,221, entitled, "Modular Computed and Direct Radiography and Method," filed on Aug. 22, 2008, which is hereby incorporated by reference in its entirety into this disclosure are preferred. Other radiography devices contemplated also include utilizing portable direct radiography detectors, including wireless versions such as ones provided by Carestream Health (DXR-1), Canon and Fuji. The scanning head 26, includes a scanning laser assembly for exciting energy stored in the storage phosphors 12 and a light collection assembly for receiving the emitted light energy.

In a preferred embodiment, the radiographic imaging system 10 also utilizes a patient table 30 that is preferably coupled to an imaging base 32. The patient table 30 is adapted for the relative movement of the patient 21 through the inner hoop assembly 13. Movement is preferably controlled through a central processing unit located in the base 32 that advantageously synchronizes the patient translation with the acquisition speed. Base 32 also preferably supports drive mechanism 20. As shown, the patient table 30 includes a frame assembly having tracks 34 for moveably supporting the imaging system 10 and particularly the base 32. Tracks 34 may be a sliding bearing surface or may include a drive assembly and track assembly or other linear translation means as is well known.

Figure 3:
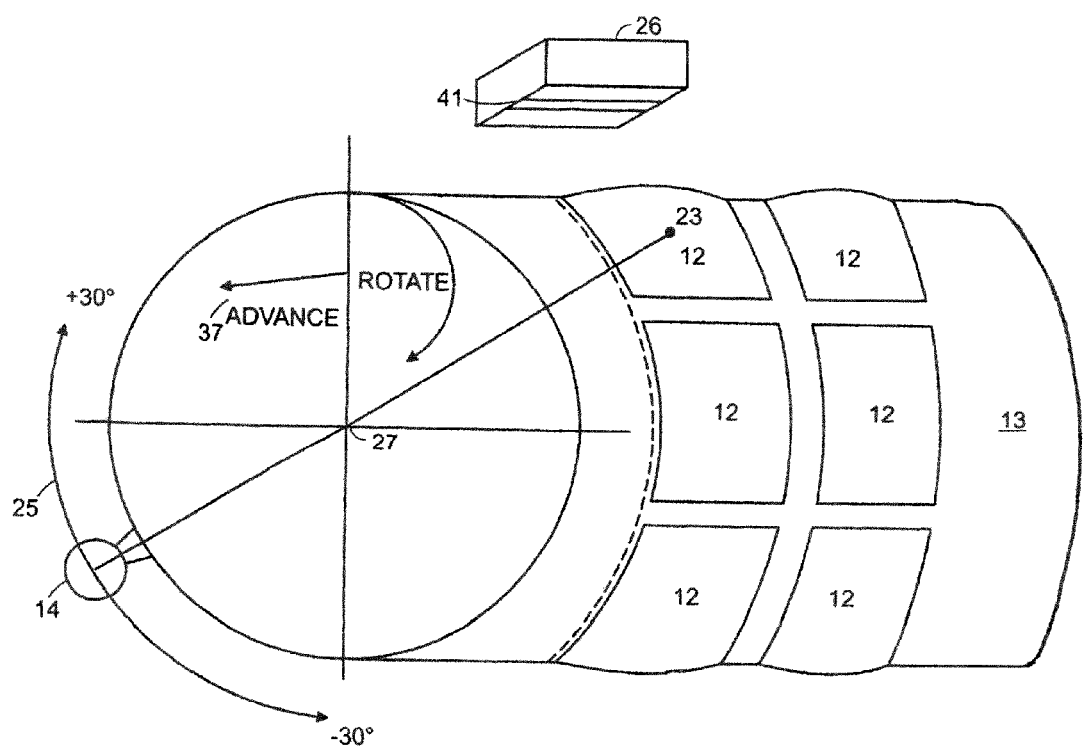
FIG. 3 is a sketch of the inner hoop assembly showing the storage phosphor surfaces on the outer surface relative to the arc of the x-ray source and the radiography device scan head.

Referring now to FIGS. 3 though 4, the radiographic imaging system 10 of the present invention is disclosed having the imaging surfaces 12 or plates positioned in a spiral or helical fashion relative to the inner hoop assembly 13. In this fashion, the x-ray beam 21 is generally acquired along a helical or spiral path enabling improved three dimensional imaging and increased acquisition efficiency. This embodiment of the present invention is referred to herein as spiral or helical tomography system 10. The spiral tomography system 10 of the present invention provides significant advantages over conventional computed radiography ("CR") and digital radiography ("DR") systems in the ability to better visualize internal anatomic structures without a significant increase in dose or cost.

The primary advantage of the present helical tomography system 10 over existing digital tomosynthesis methods is the use of storage phosphors 12 as the detector element, which enables the ability to rapidly acquire multiple projection images in near real-time, along with higher-resolution and small pixel sizes relative to most flat-panel detectors (100 microns/pixel). The present system 10 also allows for ability to use curved detector geometries plates of surfaces 12 for improved image quality.

The advantages of the spiral (helical) tomography system 10 of the present invention over conventional x-ray computed tomography ("CT") systems allow for the use of conventional x-ray tubes as the x-ray source, which lowers costs. The use of storage phosphors as the x-ray detectors 12 also lowers costs. Because only a limited number of projection x-ray images 23 are required, the present system simplifies the procedure, reduces patient 21 examination time and can significantly reduce the total dose to the patient. Moreover, reconstruction can result in potentially fewer reconstruction artifacts. The spiral tomosynthesis system 10 of the present invention significantly increases reliability and durability and has a significantly lower weight and complexity. No special training is required to set-up and calibrate the system 10 and given its relative simplicity, less specialized training is required to operate the system.

In conventional CT, the x-ray source continuously generates a collimated fan-beam of x-rays to expose a one-dimensional projection profile. For each cross-sectional image, multiple projection profiles are acquired over a 180 degree arc. In helical and spiral CT, the x-ray source rotates continuously around the patient and the patient bed is advanced continuously to acquire adjacent cross-sectional images. Additional detector arrays can be used to simultaneously acquire multiple projection profiles. Such designs require the use of expensive, high heat capacity x-ray tubes, and expensive detector arrays.

In the digital spiral tomography system 10 of the present invention the circular trajectory of an x-ray source and the helical motion an x-ray detector is utilized in order to rapidly acquire multiple, high-resolution projection images that are then used to create higher-quality reconstructed slices through a three-dimensional object (sec FIG. 3). In the preferred embodiment, an x-ray source is rotated to 7 or more acquisition positions over a 30 or 60-degree arc; in this implementation the system performs digital tomosynthesis (see FIG. 4A). In another implementation, the x-ray source can be rotated continuously around the patient and the detector gantry can be moved in a quantized helical motion in order to acquire a large number of 2D projections over a 180-degree arc; in this implementation, the system performs cone beam computed tomography (CBCT) using a limited number of views (sec FIG. 4B). In a third implementation, the x-ray source can be collimated to a fan beam, and the storage phosphor can be continuously rotated and advanced in small increments such that each 1-D projection profile is acquired as a separate line on the storage phosphor (see FIG. 4C); in this implementation, the system performs helical computed tomography (Helical CT)

Referring now to FIG. 3, the preferred embodiment of the present spiral tomosynthesis system 10 employs the circular arc trajectory of the x-ray source 14, such as an x-ray tube, along with spiral or helical motion of the storage phosphor x-ray detectors 16 in to rapidly acquire multiple, high-resolution projection images that arc then used to create higher-quality reconstructed slices through a three-dimensional object (sec FIG. 3). In the current implementation of the design, the x-ray source is rotated to 7 or more acquisition positions over a 30 or 60-degree arc; in this implementation the system performs digital tomosynthesis (see FIG. 4A). In another implementation, the x-ray source can be rotated continuously around the patient and the detector gantry can be moved in a quantized helical motion in order to acquire a large number of 2D projections over a 180-degree arc; in this implementation, the system performs cone beam computed tomography (CBCT) using a limited number of views (see FIG. 4B). In a third implementation, the x-ray source can be collimated to a fan beam, and the storage phosphor can be continuously rotated and advanced in small increments such that each 1-D projection profile is acquired as a separate line on the storage phosphor (see FIG. 4C); in this implementation, the system performs helical computed tomography (Helical CT)

Figure 4A:
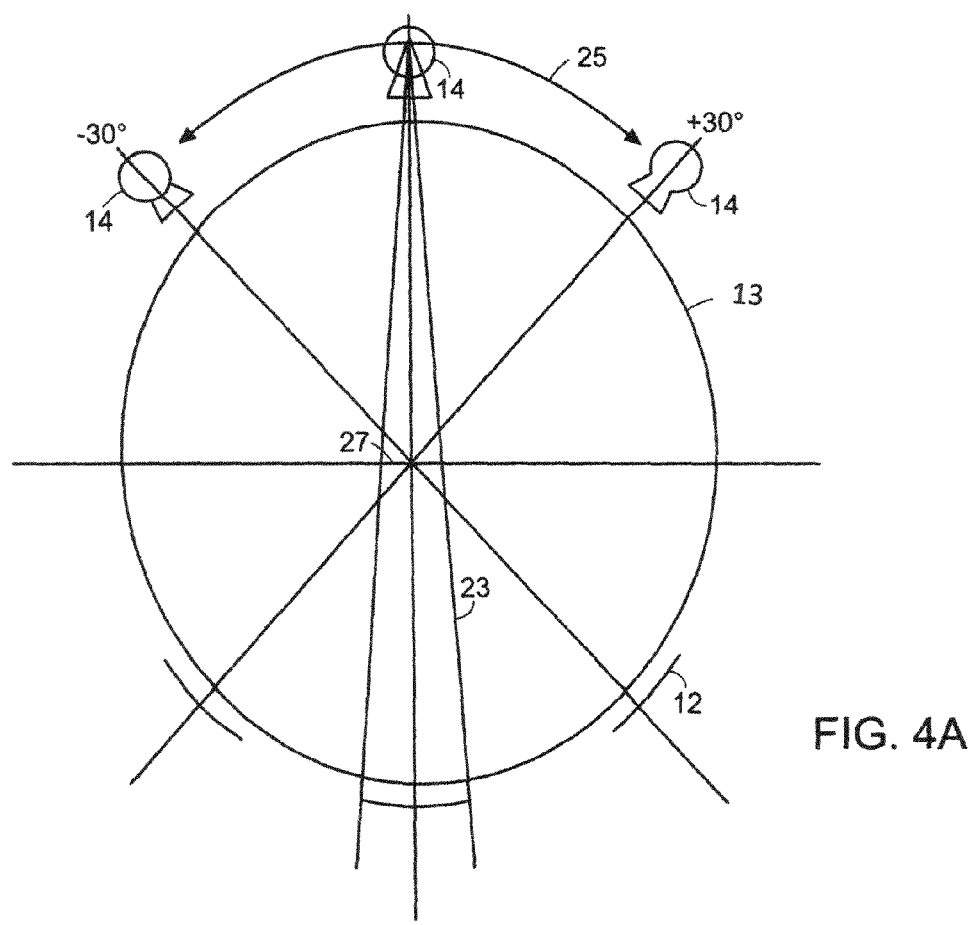
FIG. 4A is a cross sectional view of the imaging gantry assembly showing the x-ray tube and x-ray arc along with the cone beam exposure field passing through the inner hoop assembly.
Figure 4B:
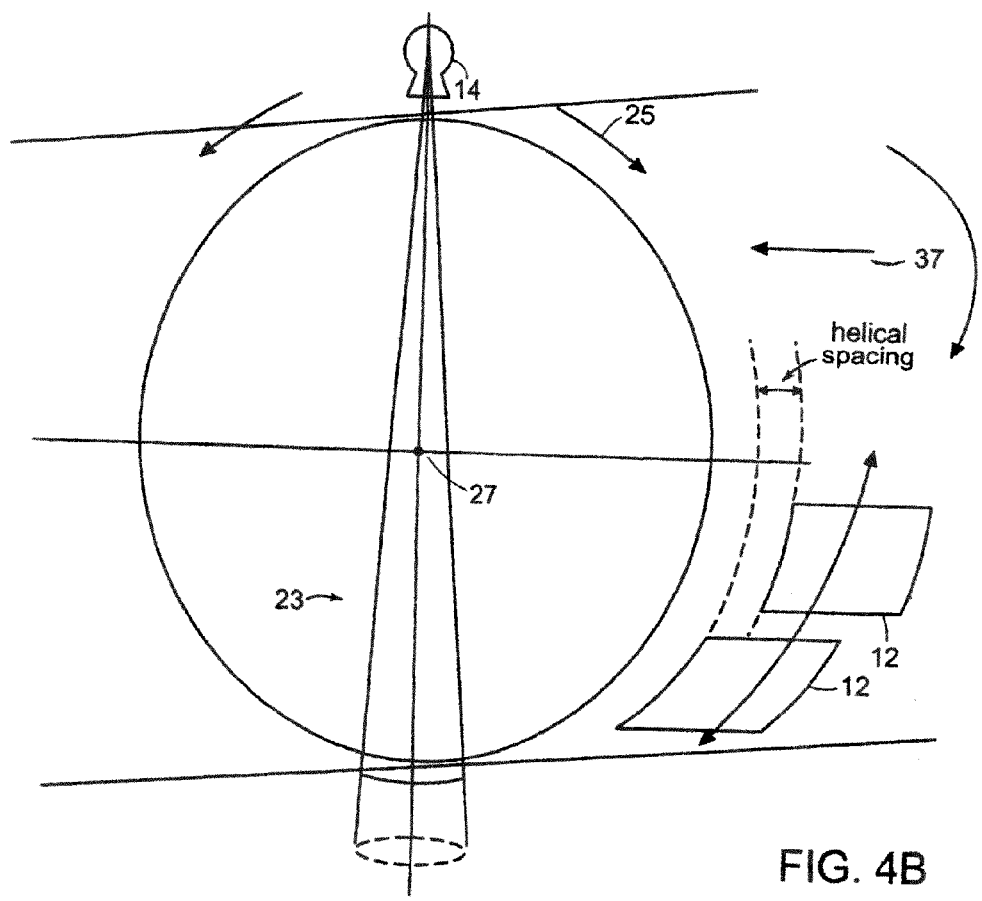
FIG. 4B is a sketch of the imaging gantry assembly showing the x-ray tube and its arc of motions along with the cone beam exposure field passing through the inner hoop assembly along with the storage phosphor surfaces.
Figure 4C:
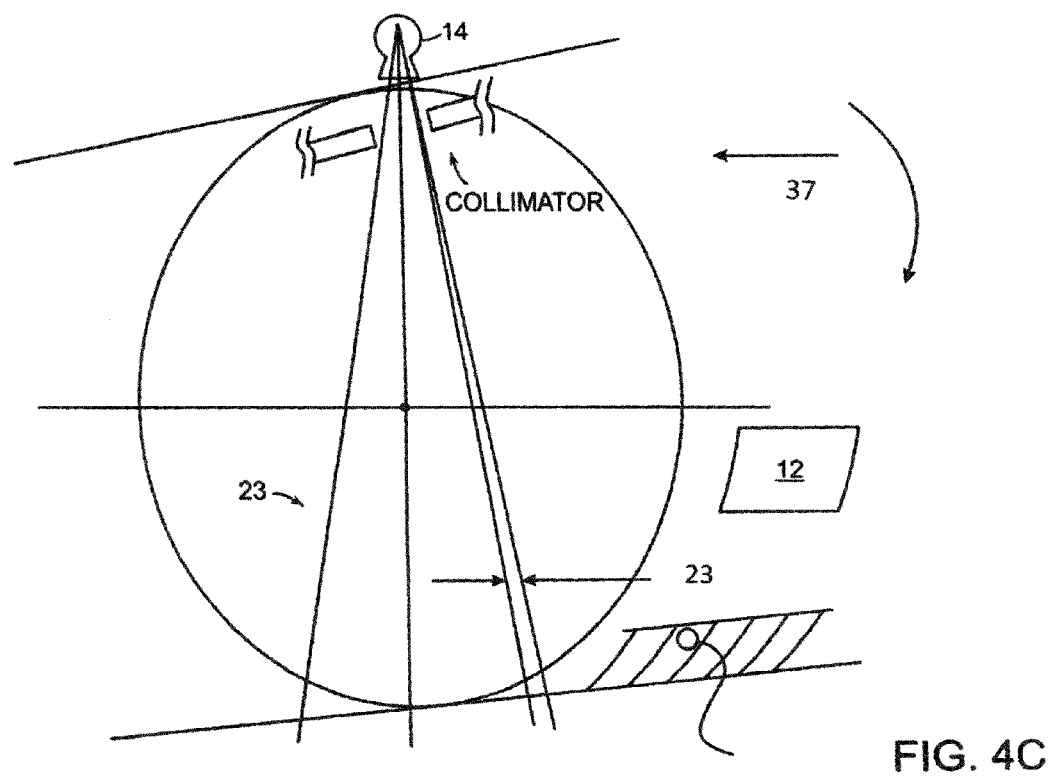
FIG. 4C is a sketch of the gantry assembly showing the x-ray tube, an x-ray collimator and the fan beam exposure field passing though the inner hoop assembly having storage phosphor coated along the exterior surface.

In the implementation of the spiral tomosynthesis system 10 illustrated in FIGS. 4A and 4B, a conventional x-ray radiation source 14 is configured to rotate around the object 21 (a patient is shown though the invention contemplate use with non destructive analysis) and collimated 27 to expose a two-dimensional area in a cone beam geometry 23. In the present digital spiral tomography, the object 21 can either be positioned at the geometric center or close to the x-ray detectors 12. A large object (e.g., a torso) positioned close to the x-ray detectors 12 to minimize magnification and enable imaging of the entire object on a standard-size phosphor. A small object (e.g., a knee or hand) can be positioned at the center in order to improve the visualization of small details as well as reduce scatter.

X-Ray Detector and Acquisition Geometry (Detector Geometry) In conventional digital Tomosynthesis, a single planar x-ray detector is typically used as the imaging detector, and a single detector is moved around the object. This limits the system to flat-panel geometry and requires that the latent image must be completely read-off the detector and the detector must be reset before the next image can be acquired. In the present digital spiral tomosynthesis system 10, multiple storage phosphor imaging plates 12 are used such that multiple imaging plates are positioned in a spiral or helical fashion around the outside surface of a tube 13. The imaging plates 13 are curved around the surface of the tube 13 or, potentially, the surface of the tube can be coated with storage phosphor material such that the entire tube becomes a large detector completely surrounding the object.

(Acquisition Geometry) For a limited number of projection views, the detector tube or hoop assembly 13 can be fixed and the x-ray source 14 can be rotated to a limited number of positions (within the designated arc as shown in FIG. 4) such that each position corresponds to one view and each projection is acquired on a different region of the detector tube (as shown in FIG. 3). The x-ray source 14 is rotated to each position (in a 60-degree acquisition are) and, at each position, a projection x-ray image is exposed onto the corresponding imaging plate 12.

In order to increase the number of projection views, the x-ray source 14 can be rotated to an increased number of positions and, as the x-ray source rotates to the next position, the detector tube gantry 11 is advanced and rotated in a spiral or helical fashion. Each rotation of the detector tube 13 exposes a different region of the storage phosphor 12 such that a large number of projections can be acquired in a very short period of time (as shown in FIG. 4).

Figure 5A:
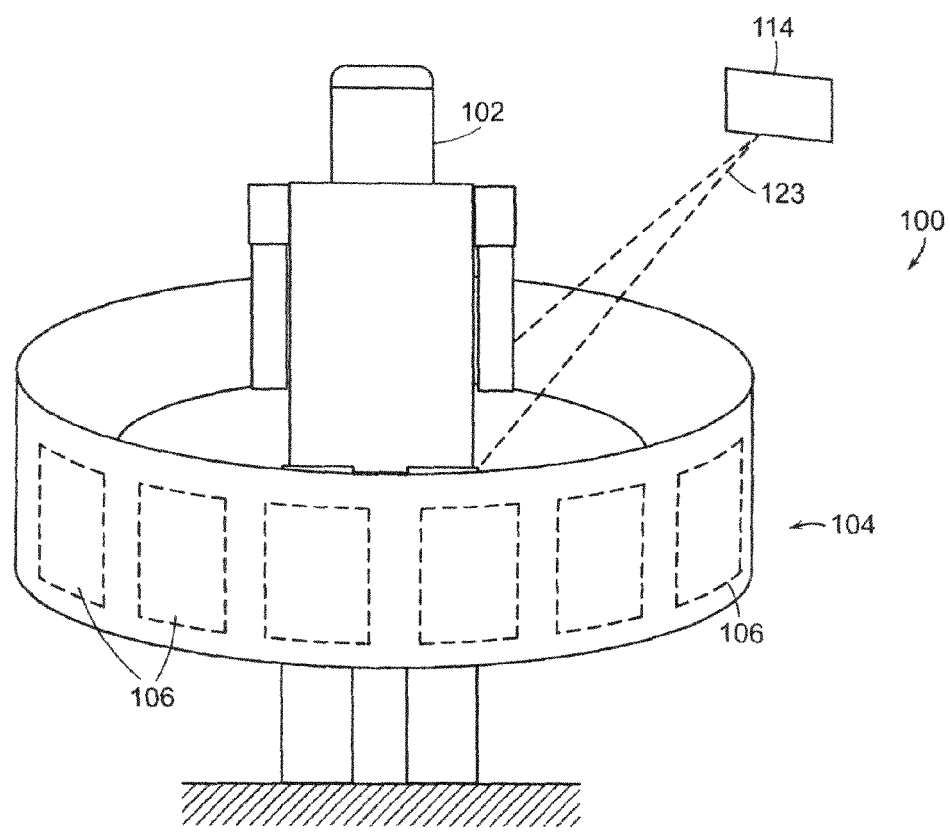
FIG. 5A shows a patient standing in a weight bearing position within the tubular cavity of an embodiment of the present invention.
Figure 5B:
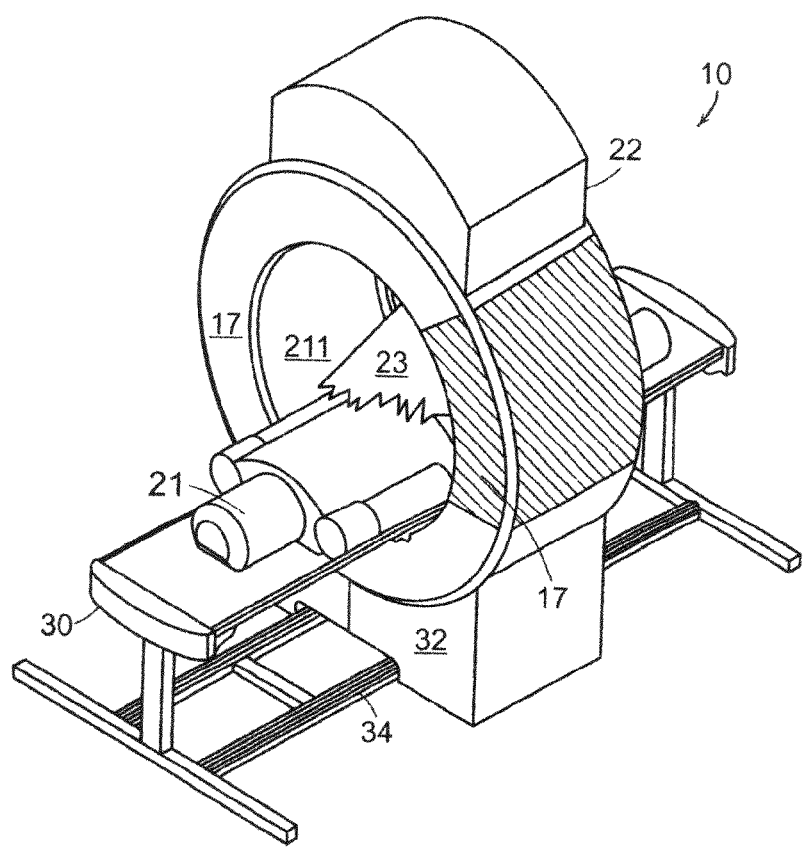
FIG. 5B is a perspective view of an embodiment of the present invention showing a cut away view of a section of the gantry housing assembly.
Figure 6A:
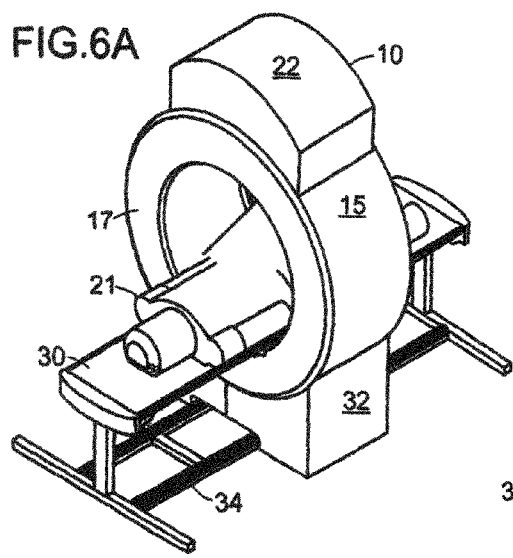
FIGS. 6A through 6D show different perspectives of an embodiment of the present invention.
Figure 6B:
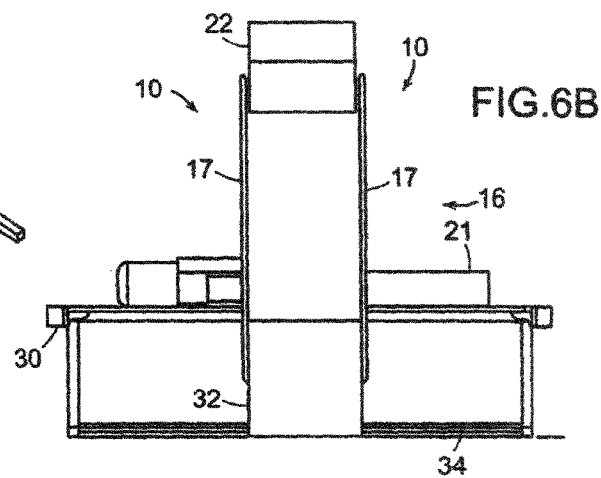
Figure 6C:
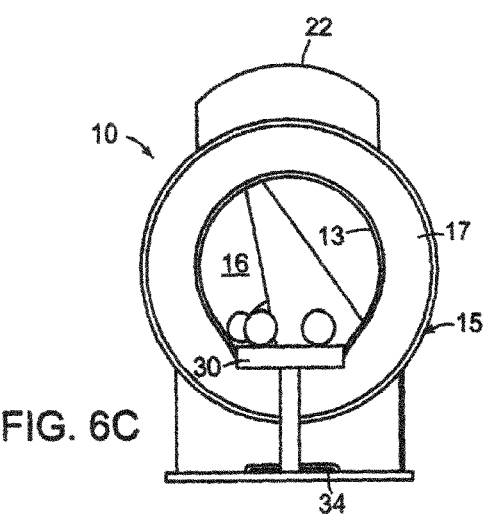
Figure 6D:
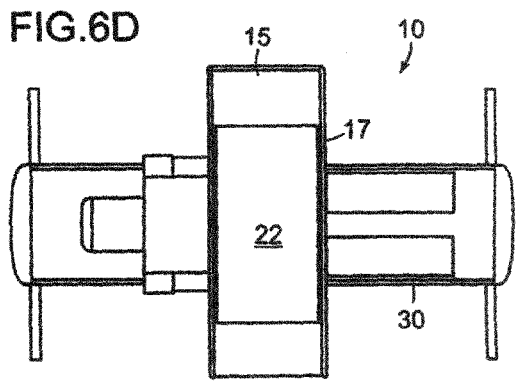

(Acquisition Detector Tube Gantry 11) In one implementation of the acquisition detector tube gantry for the present digital helical Tomosynthesis system 10, it is possible to orient the acquisition gantry 13 sideways such that the patient 21 can be sitting upright or standing rather than lying on an acquisition table 30 (see FIG. 5A). In another implementation of the acquisition gantry 11 (and specifically 13), it is possible to create a C-shaped semi-circular gantry such that a patient bed 30 can slide laterally into the imaging hoop 11 or the scanning imaging hoop 11 can be oriented such that the patient can walk upright into the scanner (see FIGS. 5B and 5C).

Image Readout

After all of the projections have been exposed, the detector tube gantry 13 is rotated back to the home position and the projection x-ray images are acquired by scanning the storage phosphor 12 as it is rotated back to the home position. The latent image on the storage phosphor 12 or each of them, is read-out using a scan head module 26 (illustrated in FIG. 2). The scan head module 26 consists of a low-power laser to stimulate the emission of light from the excited regions of the storage phosphors 12, an oscillating mirror to progressively scan the laser across a scan line, a light-collection cylinder to collect the light emitted by the phosphor, one or more photomultiplier tubes (PMTs) to convert the collected light into an electronic signal, and an analog-to-digital (A/D) conversion circuit and amplifier to convert the electronic signal into a digital picture element (pixel). The unique design of the present digital spiral tomography system 10 enables the use of a single, high-resolution, light-weight, low-cost scan head module, or the use of multiple scan head modules to decrease the time required to read-out multiple projections.

Image Reconstruction

Different tomosynthesis reconstruction algorithms were used to reconstruct tomographic cross-sections from the acquired projection images. The commonly used reconstruction algorithms include: Shift and Add (SA)—Tomosynthesis; Filtered hack-projection (FBP)—Tomosynthesis; Spiral CT; Cone Beam CT; Algebraic reconstruction techniques (ART)—Tomosynthesis; Spiral CT; Cone Beam CT. Depending upon the acquisition geometry, the appropriate reconstruction algorithm is used to either construct tomosynthesis images or true cross-sectional images from a limited number of 1-D or 2-D projections.

The spiral tomosynthesis system 10 of the present invention can be used in a variety of clinical applications. These include, but are not limited to: mammography; thoracic imaging (chest); lung tumor screening; screening for tuberculosis as well as orthopedic imaging for evaluation of fractures; evaluation of vertebrae for spinal fusion surgery; evaluation of knee injuries; as well as evaluation of arthritis and other joint disease; evaluation for surgical planning of implants.

Referring now back to FIG. 5A, an alternative embodiment of the spiral tomography system 100 of the present invention is oriented along a vertical axis. In this embodiment, the acquisition gantry 104 is oriented sideways such that the patient 102 can be sitting upright or standing rather than lying on an acquisition table. The patient 102 may be placed against a vertical table or support (not shown). This embodiment of the spiral tomography system 100 enables the acquisition of images under clinically-realistic breathing and weight-hearing conditions. Storage phosphor surfaces 106 capture the x-ray exposure beam similarly to previously disclosed embodiments.

General Overview of System (Basic Concept) The imaging system 10 of the present invention operates similarly the computed radiography devices made by Icrco. Inc. of Torrance Calif., such as the iDR or 3600 products. In general, an Imaging Plate, or IP, receives and stores patient information (x-ray) and the information is retrieved using a scanning head assembly 26. An inner hoop or hoop assembly 13 of approximately 43 inches in diameter (though it need not necessarily be cylindrical) holds several storage phosphor plates 12 such as 14 inch by 17 inch plates readily available and used in computed radiography. The plates 12 are placed along the exterior face of the inner hoop assemblies 13. These plates 12 store imaging information, similar to their function in a computed radiography system. The scanning mechanism 26, similar to the one currently utilized in the ICRCO, iDR product, remains fixed within the hoop or gantry housing 11 (although the scanner translates in an alternative embodiment and in another, multiple scanners arc used). The inner cylinder or hoop 13, to which the phosphor plates 12 are secured, rotates axially such that the scanning mechanism 26 is able to read and erase the storage plates 12 in a similar fashion to that known in the art.

The storage plates 12 are exposed using a radiation source similar to that used in standard radiography. The radiation source 14 mounts to a track system 24 (FIG. 7) at the top of the gantry assembly 11. The x-ray track system 24 allows the tube 14 to rotate about the center axis of the machine and defines an arc. This allows for the acquisition of imaging information from various x-ray angles. After each exposure 23 the inner hoop 13, which holds the plates 12, is rotated to position an unexposed plate under the patient 21. Lead, or a similar attenuating medium may be used to protect unexposed plates or phosphor surfaces 12 from x-ray scatter. After all the plates 12 have been exposed, the imaging information is extracted using the scan head assembly 26.

The entire hoop structure 11 mounts to a track or runner system 34 allowing for image acquisitions along the entire table 30 length 37 (FIG. 1).

The presently preferred embodiment of the spiral tomosynthesis system 10 of the present invention provides the ability to expose patients and acquire images in under 3 minutes. Patients will be required to spend as short a time as possible in the machine, with a range between 30 seconds to a minute. Current tomosynthesis and CT systems utilize different image capturing technology, are more complex and disadvantageously slower. Moreover, traditional tomosynthesis systems require image acquisition after each x-ray exposure, while utilizing a DR panel to acquire the images, which further requires calibration before each exposure.

Referring now to FIGS. 10 through 13, a preferred embodiment of the computed tomosynthesis system 200 of present invention is shown. In this embodiment, the computed tomosynthesis system 200 includes a gantry housing assembly 211 defining a tubular inner cavity 216 within a cylindrical inner hoop assembly 213. Gantry housing 211 is supported by a base member 232. The gantry housing 211 and base member 232 are adapted to support a patient support table 230 that is moveable along an axis 27 that runs perpendicular to the tubular cavity 216 and is generally concentric with the inner hoop assembly 211. The gantry assembly 211 also includes an outer hoop assembly 215 that is generally concentric with and positioned outside of and spaced apart from the inner hoop assembly 213. As noted in the previously described embodiments, the gantry assembly 211 may include an inner cylindrical cover to cover and protect the inner hoop assembly 213 as well as an outer cylindrical cover 229 that are coupled to sides 17 and adapted to cover and protect all internal and moving components.

Figure 12:
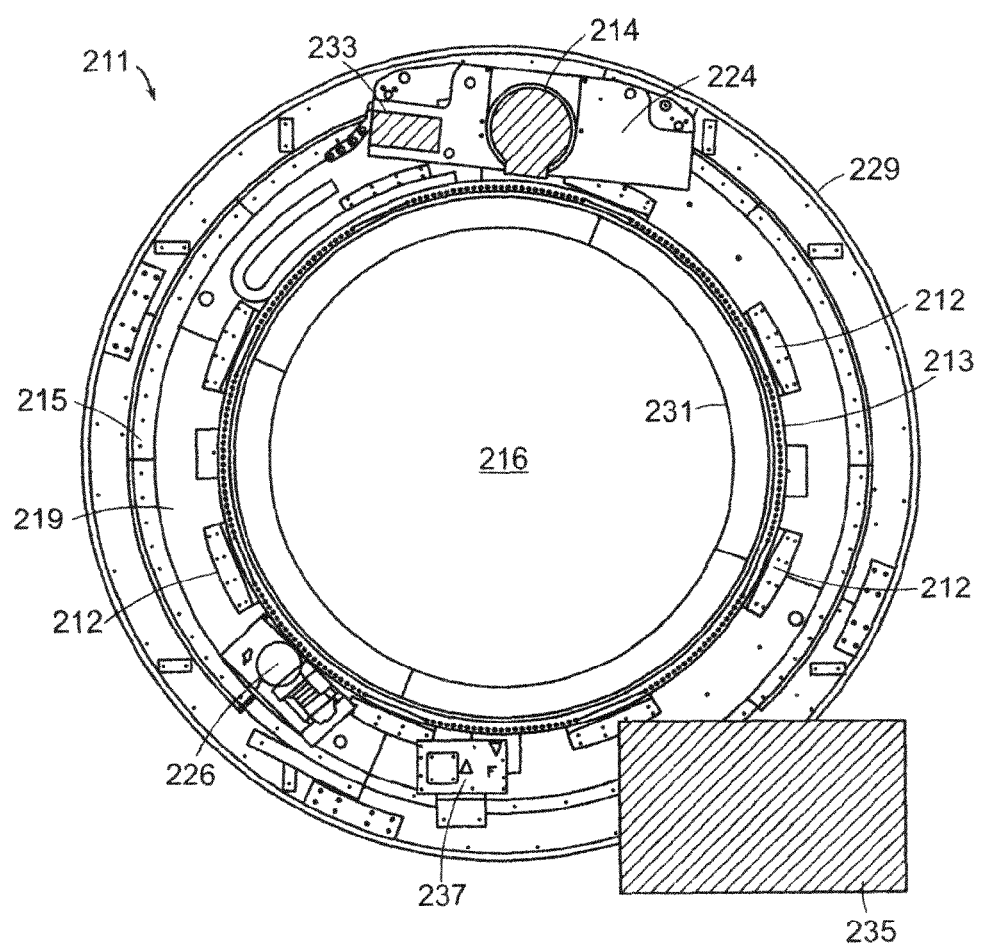
FIG. 12 shows a cross-sectional view of the gantry assembly of the embodiment of the present invention shown in FIG. 10.
Figure 13A:
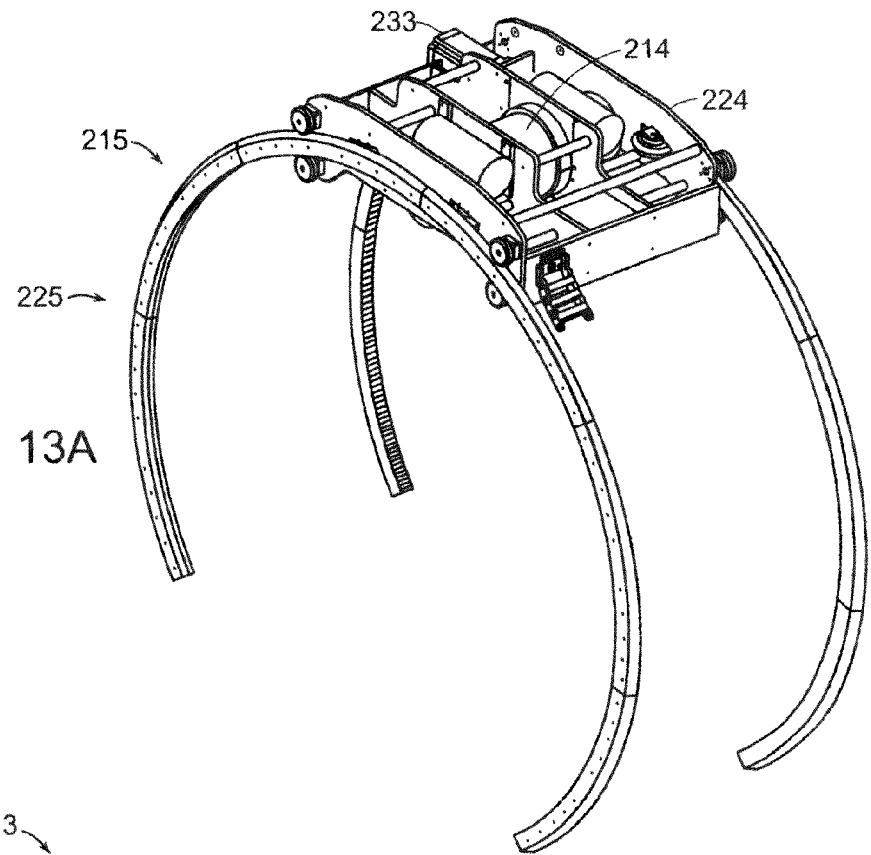
FIG. 13A shows a perspective view of an embodiment of the outer hoop assembly, including the x-ray source support housing and travel assembly.
Figure 13B:
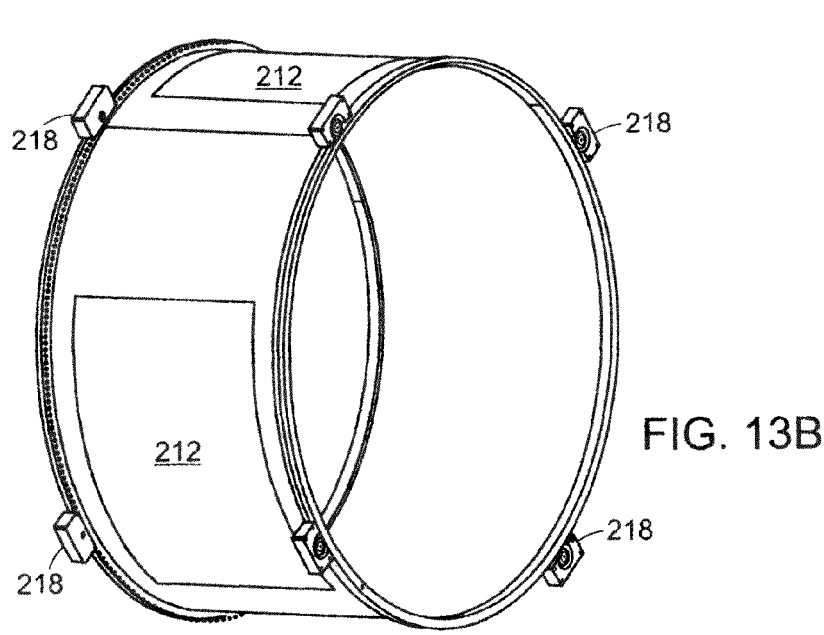
FIG. 13B shows a perspective view of an embodiment of the inner hoop assembly.

Referring now to FIGS. 12 and 13, the gantry assembly 211 of this preferred embodiment, includes an x-ray source 214 that is positioned between the inner hoop assembly 213 and the outer hoop cover 229. The x-ray source 214 is preferably part of an x-ray assembly and positioning assembly 224. The x-ray assembly 224 is adapted to position the x-ray source 214 along the outer hoop assembly track 215 so as to expose the desired location of the object. The x-ray assembly 224 preferably includes a drive means 234, such as an electric motor. The drive motor 234 is adapted to move the x-ray source 214 along the outer hoop track 215 shaped into the arc 225. The x-ray source is electrically coupled to an x-ray generator 235.

While described for use with patients, and namely human patients, the imaging device of the present invention may similarly be adapted for use with animals, such as in a veterinary setting, for use in non destructive testing or even with security screening.

The foregoing description of the embodiments of the invention has been presented for the purposes of illustration and description. It is not intended to be exhaustive to limit the invention to the precise forms or methods disclosed. Persons skilled in the relevant art can appreciate that many modifications and variations are possible in light of the above teaching.

What is claimed is:

1. A computed tomography system comprising:
   (a) a housing assembly defining a tubular cavity about a perpendicular axis;
   (b) a tubular outer hoop assembly mounted within the housing about the perpendicular axis;
   (c) a tubular inner hoop assembly supporting a plurality of spaced apart x-ray photostimulable detector members, the inner hoop assembly rotatably coupled to the housing about the perpendicular axis and inside the outer hoop assembly;
   (d) an x-ray source adapted to expose an object within the tubular cavity with x-ray energy, the x-ray source moveably coupled to the outer hoop assembly and adapted to move about a common arc with the outer hoop assembly and expose objects located within the tubular cavity;
   (e) a computed radiography device mounted within the housing between the inner hoop assembly and the outer hoop assembly and adapted for scanning at least one of the x-ray detector members and for acquiring x-ray energy from the detector members and wherein said computer radiography device utilizes a scan head for such scanning;
   (f) a first drive apparatus adapted for rotating the detector means about the tubular cavity relative to the radiography device;
   (g) a second drive apparatus adapted for moving the x-ray source along the common arc about the tubular cavity;
   (h) wherein the inner hoop and x-ray source are independently rotatable about the tubular cavity to expose the object with x-rays from a plurality of perspectives; and
   (i) wherein when the inner hoop assembly is rotated relative to the housing, the detector members are rotated relative to and adjacent the radiography device allowing the radiography device to acquire any retained x-ray exposure energy from the adjacent detector member.

2. The computed tomography system of claim 1 wherein the photostimulable detector members comprise a plurality of photostimulable plates secured to an outer surface of the inner hoop assembly.

3. The computed tomography system of claim 2 wherein the computed radiography device is adapted to erase the x-ray energy stored in at least one of the photostimulable plates.

4. The computed tomography system of claim 2 wherein the computed radiography device is adapted to function as a direct radiography system.

5. The computed tomography system of claim 2 wherein the computed radiography device is fixed to the housing and the inner hoop assembly rotates at least one detector member adjacent the scan head.

6. The computed tomography system of claim 5 wherein the object is exposed to x-ray energy from the x-ray source at substantially the same time that the computed radiography device is scanning a detector member.

7. The computed tomography system of claim 1 wherein the detector members comprise a plurality of photostimulable plates mounted within cassettes that are removeably secured to the inner hoop assembly.

8. The computed tomography system of claim 1 wherein the detector members comprise a plurality of digital detector panels secured to the inner hoop assembly.

9. The computed tomography system of claim 1 wherein the inner hoop assembly rotates about the tubular cavity at a different speed than the x-ray source rotates about the tubular cavity.

10. A computed tomosynthesis system comprising:
    (a) a tubular gantry assembly having a cylindrical inner hoop assembly positioned within a larger outer cylindrical hoop assembly and a plurality of side plates coupling the inner and outer hoop assemblies and defining a cylindrical cavity there between, the gantry assembly adapted for receiving and passing an object within a tubular cavity defined inside the inner hoop assembly;
    (b) an x-ray source coupled to said outer hoop assembly and adapted for emitting x-ray energy through an object placed within the tubular cavity;
    (c) a plurality of spaced apart photostimulable storage phosphor surfaces coupled to an outer surface of the inner hoop assembly and adapted to receive the x-rays passing thought the object;
    (d) a computed radiography device having a scan head, the computed radiography device coupled to the gantry assembly between the inner hoop and the outer hoop and adapted for scanning the storage phosphor surfaces to acquire images from the stored x-ray energy;
    (e) an inner hoop drive assembly adapted to rotate the phosphor surfaces about the tubular cavity and relative to the scan head wherein the computed radiography device can acquire the stored x-ray energy; and
    (f) an x-ray source drive adapted to move the x-ray source about an arc having a common perpendicular axis with the tubular cavity; and
    (g) wherein the inner hoop assembly is rotatable about the tubular cavity and relative to the outer hoop assembly.

11. The computed tomosynthesis system of claim 10 wherein the photostimulable storage phosphor surfaces a needle phosphor.

12. The computed tomosynthesis system of claim 10 wherein the computed radiography device and the storage phosphor surfaces are adapted for use in non-destructive testing.

13. The computed tomosynthesis system of claim 10 wherein the x-ray source is moveable about an arc having a rotational axis in the tubular cavity such that x-ray exposures can be taken of the object from a plurality of locations along the arc.

14. The computed tomosynthesis system of claim 10 wherein the object is exposed to x ray energy from the x-ray source at substantially the same time that the computed radiography device is scanning a storage phosphor surface.

15. The computed tomosynthesis system of claim 10 wherein at least one of the storage phosphor surfaces comprises a needle phosphor compound.

16. The computed tomosynthesis system of claim 10 wherein the scan head passes over the storage phosphor surfaces to acquire images from the stored x-ray energy and wherein the scan head comprises an outer housing supporting a light collection assembly and an optical assembly.

17. The computed tomosynthesis system of claim 16 wherein the scan head is coupled to the gantry assembly such that storage phosphor surfaces may be scanned when the inner hoop is rotated by the inner hoop drive assembly.

18. The computed tomosynthesis system of claim 16 wherein the scan head is moveable relative to the inner hoop assembly so that the storage phosphor surfaces may be scanned while x-ray exposure is occurring onto other phosphor storage surfaces.

19. The computed tomosynthesis system of claim 10 wherein the storage phosphor is coated directly onto the surface of the inner hoop.

20. The computed tomosynthesis system of claim 10 wherein the storage phosphor comprises curved storage phosphor plates coupled to the curved outer surface of the inner hoop assembly.

* * * * *